(12) United States Patent
Johnson

(10) Patent No.: US 8,752,799 B2
(45) Date of Patent: Jun. 17, 2014

(54) MOVABLE AND ADJUSTABLE COOLER STAND

(76) Inventor: Sheila Elaine Johnson, Houston, TX (US)

( * ) Notice: Subject to any disclaimer, the term of this patent is extended or adjusted under 35 U.S.C. 154(b) by 0 days.

(21) Appl. No.: 13/272,153

(22) Filed: Oct. 12, 2011

(65) Prior Publication Data

US 2012/0211612 A1 Aug. 23, 2012

Related U.S. Application Data

(63) Continuation-in-part of application No. 11/321,432, filed on Dec. 29, 2005, now abandoned, and a continuation-in-part of application No. 11/072,093, filed on Mar. 4, 2005, now abandoned.

(51) Int. Cl.
*A45D 19/04* (2006.01)
*F16M 11/00* (2006.01)
*A47F 7/00* (2006.01)

(52) U.S. Cl.
USPC .......... 248/127; 248/128; 248/129; 220/4.22; 220/592.18; 220/475; 220/4.23; 602/1; 602/2; 602/14; 211/85.13

(58) Field of Classification Search
USPC ............ 248/129, 127, 128; 220/4.22, 592.18, 220/475, 4.23; 602/1, 2, 14; 211/85.13
See application file for complete search history.

(56) References Cited

U.S. PATENT DOCUMENTS

| | | | | | |
|---|---|---|---|---|---|
| 396,459 | A | * | 1/1889 | Bertrand | 47/66.1 |
| 1,396,445 | A | * | 11/1921 | Loudon | 248/154 |
| 1,609,246 | A | * | 11/1926 | Hamburger | 47/39 |
| 2,003,986 | A | * | 6/1935 | Witthuhn | 47/39 |
| 4,725,027 | A | * | 2/1988 | Bekanich | 248/125.8 |
| 5,094,415 | A | * | 3/1992 | Revette et al. | 248/133 |
| 5,277,695 | A | * | 1/1994 | Johnson et al. | 602/14 |
| 5,487,476 | A | * | 1/1996 | Barfield | 211/85.23 |
| 5,507,792 | A | * | 4/1996 | Mason et al. | 607/104 |
| 5,598,662 | A | * | 2/1997 | Droste | 47/39 |
| 6,877,276 | B1 | * | 4/2005 | Legunn et al. | 47/65.5 |
| 7,293,748 | B1 | * | 11/2007 | Hoser | 248/146 |
| 2005/0075592 | A1 | * | 4/2005 | Garon | 602/2 |
| 2006/0283852 | A1 | * | 12/2006 | Greiner | 220/4.22 |
| 2012/0211612 | A1 | * | 8/2012 | Johnson | 248/74.1 |

* cited by examiner

*Primary Examiner* — Terrell McKinnon
*Assistant Examiner* — Christopher Garft
(74) *Attorney, Agent, or Firm* — Delphine James

(57) ABSTRACT

The present invention discloses a stand for a cooler containing cooling solution. The cooler further includes an attached flexible tubing outlet for draining the cooling solution through the flexible tube outlet into a medical cuff for reducing swelling of injured tissue. The stand further comprises a cylindrical container with a cavity for receiving through the opened top end of the lateral sidewall the cooler therein. An elongated pedestal is further defined by a top end and a bottom end. The top end of the pedestal is attached underneath the bottom side of the container. The container is supported in an upright position a distance above the surface of the ground. An aperture is located in the lateral side wall for receiving the flexible tubing outlet therethrough.

19 Claims, 15 Drawing Sheets

MOVABLE AND ADJUSTABLE COOLER STAND

This patent is a continuation in part of patent application Ser. No. 11/072,093 filed Mar. 4, 2005, now abandoned and Ser. No. 11/321,432 filed Dec. 29, 2005, now abandoned.

BACKGROUND

This version of the invention is concerned with the field of therapeutic cooling devices. More specifically, this version of the invention is concerned with a movable and adjustable stand that houses an medical cast cooler in proximity to an medical cast worn by a user in order to provide the medical cast with a continuous supply of cooling solution.

PRIOR ART

People who are recovering from various injuries, such as broken or fractured bones, trauma, tears, or sprains to muscles and other tissue, use an medical cast to support the injured body area to aid in healing of the damaged body part. The medical cast comprises a cuff that is wrapped around the damaged body part and is inflated to a specific pressure to provide resistance against the damaged body part as an aid in healing, such as ensuring proper alignment of a broken or fractured bone or to support damaged tissue and control swelling and inflammation. The medical cast used in connection with this invention also contains means whereby a cooling solution can be introduced into the interior of the cuff of the medical cast and circulated throughout channels, pockets, or bladders in the medical cast so as to provide cold and compression therapy. In the industry, Aircast manufactures this type of medical cast. However, the present invention is not limited to Aircast. This type of therapy is crucial in treating damaged, sprained, stressed, or inflamed tissue. The cooling solution is typically ice water, and such solution is stored within an special medical cast cooler, jug, or similar storage device. A typical medical cast cooler is comprised of an insulted, cylindrical container enclosing a storage cavity, lid or cover releasably attached to the container over a top aperture thereof, grasping handle connected to the container, and a flexible tube or hose of varying length. The flexible tube is attached at a first end at or near the bottom of the container and at a second end to the medical cast cooler. The medical cast cooler may have a control valve or spigot that releases cooling solution from the container to the flexible tube.

When the flexible tube is connected to the container and the medical cast, cooling solution is transported from the container, through the tube, and into the medical cast. The cooling solution, maintained in the medical cast and directly over the injured body part, provides the necessary application of cold and compression therapy to enhance healing.

Although the use an medical cast cooler to deliver cooling solution to an medical cast provides a therapeutic effect, several disadvantages and drawbacks result from such an arrangement. For instance, if the user desires to move about while the medical cast cooler is connected to the medical cast, the user must physically transport the medical cast cooler, such as carrying the cooler by the handle. This option for the most part is infeasible as the medical cast cooler, filled with cooling solution, presents significant weight and bulk and cannot be transported or carried by a user nursing a damaged body part. Alternately, the user can enlist the aid of another person to hold or carry the medical cast cooler, who may not always be available or agreeable for such a task. The user could also fashion or use various makeshift support and transport devices, such wheeled carts, dollies, and the like. However, such devices do not support the medical cast cooler at the proper height in relation to the medical cast, which is necessary to ensure adequate and uninterrupted flow of cooling solution, nor do such devices provide the stability necessary to prevent the medical cast cooler from being toppled or turned over in the case if the medical cast or flexible tube is suddenly impacted.

What is needed then to overcome the aforementioned disadvantages of storing or supporting an medical cast cooler while said cooler is connected to an medical cast is the provision of a movable and adjustable stand for medical cast cooler. Such a cooler stand would support an medical cast cooler above a floor, ground, or support surface and contain means to allow the stand to be moved about over the floor, ground, or support surface without being toppled or tipped over during use, and to be adjusted in height so that the medical cast cooler can be aligned in the most optimum position with respect to an medical cast while the medical cast cooler is connected thereto.

DISCUSSION OF THE PRIOR ART

Numerous devices for supporting therapeutic and medical apparatuses in close proximity to a user or patient have been provided in the prior art. Even though these devices may be suitable for the specific individual purposes to which they address, they would not be suitable for the purposes of the present version of the invention, as such devices are generally intended to support an apparatus, such as a container for intravenous solution, connected to a patient who is generally immobile or stationary. These devices are exemplified by U.S. Pat. No. 4,541,596, Portable Intravenous Pole For Use In An Emergency, issued to Price on 17 Sep. 1985; U.S. Pat. No. 4,744,536, Collapsible Pole And Stand Combination, issued to Bancalari on 17 May 1988; U.S. Pat. No. 5,344,169, Multi-Pole Support Stand, issued to Pryor et al. 6 Sep. 1994; and U.S. Pat. No. 6,182,662, Intravenous Transport/Support Device, issued to McGhee on 6 Feb. 2001.

As such, it may be appreciated that there is a continuing need for a new and improved stand for storing and supporting an medical cast cooler in proximity to a user or patient wearing an medical cast while said medical cast cooler is connected to said medical cast. Such an medical cast cooler stand will support the medical cast cooler at a height and position that optimizes the flow of cooling solution from the cooler to the medical cast and provide the optimum stability the prevents the stand and medical cast cooler from being toppled in the case of a sudden impact impinging upon the flexible hose or stand while ensuring that the flexible hose does not become disconnected from the medical cast and medical cast cooler. In these respects, the present version of the invention substantially departs from the conventional concepts and designs of the prior art, and in so doing provides an apparatus that substantially fulfills this need. Additionally, the prior patents and commercial techniques do not suggest the present inventive combination of component elements arranged and configured as disclosed herein.

The present invention achieves its intended purposes, objects, and advantages through a new, useful and unobvious combination of method steps and component elements, with the use of a minimum number of functioning parts, at a reasonable cost to manufacture, and by employing only readily available materials.

SUMMARY

The present version of the invention, which will be described in greater detail hereinafter, relates to the field of therapeutic cooling devices. More specifically, this version of the invention is concerned with a movable and adjustable stand that houses an medical cast cooler in proximity to an medical cast worn by a user in order to provide the medical cast with a continuous supply of cooling solution. My version of the invention overcomes all of the shortcomings listed previously, in addition to novel aspects that will be described in detail hereinafter.

Described briefly, according to a typical embodiment, the invention presents an adjustable and movable stand for medical cast cooler. The stand supports an medical cast cooler containing cooling solution above a floor, ground, or support surface so that the cooling solution contained within the cooler can be delivered to an medical cast being worn by a user or patient in need of cold and compression therapy. The stand can be adjusted in height to align the medical cast cooler so as to provide the optimum height or alignment of the medical cast cooler with respect to the medical cast or patient and can be moved about over a floor, ground, or support surface should a user or patient desire to be ambulatory.

The stand is comprised of a cylindrical container and a pedestal, said container attached to the top end of the pedestal. The container, which has an open top and encloses an interior space or cavity, is further comprised of a continuous lateral sidewall and a disc-shaped bottom sidewall. The lateral sidewall is surrounded by a first band located at the top edge of the lateral sidewall and by a second band located at the medial section of the lateral sidewall. The lateral sidewall is bisected into first and second sidewall members, and the bands are bisected into two band sections. The sidewall members are attached to each other at cooperating edges by hinges located on adjoining ends of the band sections. The first sidewall, hingedly attached to the second sidewall member, can be pivoted upon said hinges with respect to the second sidewall member, bottom sidewall. An aperture which remains attached to the is located within the first sidewall member proximate to the junction of the first sidewall member of the lateral sidewall and bottom sidewall.

The pedestal is comprised of an upright tubular assembly and a base. The tubular assembly is further comprised of a lower tubular member, locking collar, and upper tubular member with the upper tubular member telescopically engaged within the lower tubular member and maintained in position within said lower tubular member by the locking collar. The bottom sidewall of the container at the bottom surface thereof is attached to the top end of the upper tubular member. The base consists of a central hub, which is attached to the lower end of the lower tubular member and two cross members, said cross members disposed in perpendicular relation to each other. Wheels are located within the underside of the cross members at opposed ends thereof.

During use of the stand, an medical cast cooler is situated within the container of the stand, resting upon the bottom sidewall of the container and surrounded by the lateral sidewall. The flexible tube of the medical cast cooler is passed through the aperture of the first sidewall member of the container and extends for some distance therefrom to connection with an medical cast. As necessary, the height of the container and medical cast cooler positioned therein can be adjusted with respect to a floor, ground, or support surface and an medical cast to which the cooler is connected by extending or retracting the upper tubular member within the lower tubular member and securing the upper tubular member in place by means of the locking collar. Additionally, the stand can be positioned at various locations upon a floor, ground, or support surface by wheeling the stand upon the wheels of the base.

The cooler stand can be customized or adapted with various accessories. For instance, the height of the lateral sidewall of the container can be increased by use of a second sidewall, which is inserted within the lateral sidewall. The second or extensible sidewall engages the 'lateral sidewall in slight frictional engagement and can be raised or lowered as necessary to accommodate medical cast coolers of varying size and capacity. Similarly, an medical cast cooler can be secured in place within the container and prevented from moving or being relocated within the container by inserting one or more flexible, resilient pads within the container between the inside surface of the lateral sidewall and cooler. To aid the base in supporting the tubular assembly and container in upright alignment, an outrigger stand can be detachable positioned upon the lower tubular member. The outrigger stand is comprised of a central collar, which receives the lower tubular member, four leg members pivotally attached to the collar, and four foot members, each of which is pivotally attached to a cooperating leg member. The foot members extend beyond the cross members and make contact with a floor, ground, or support surface so that the outrigger stand 'can augment the base in stabilizing the cooler stand. A sensor with audible and visual alarm is attached to tubular assembly to signal a user should the cooler stand deviate from the upright or optimum position.

A swivel hinge on one side thereof is attached to the top of the upper tubular member and on a second side thereof to the bottom surface of the bottom sidewall of the container. As such, the container will rotate with respect to the pedestal to re-orient the container and medical cast cooler stored therein if the medical cast, connected to the cooler, varies its position so that the medical cast cooler and flexible tube remain properly aligned with the medical cast. Additionally, alignment of the flexible tube can be adjusted, varied, re-oriented, or secured in place with use of a tube support arm. The tube support arm consists of a first collar detachably secured around the upper tubular member, first arm, second arm, and second collar. The first arm is pivotally attached at a first end to the first collar and at a second end to a first end of the second arm. The second arm at a second end thereof is attached to the second collar. As such, the first and second arms, and second collars can be pivoted with respect to each other and the first collar secured to the upper tubular member. The flexible tube extending from the medical cast cooler is disposed within the second collar, which maintains the flexible tube a position necessary to facilitate delivery of cooling solution from the medical cast cooler through the flexible tube to the medical cast.

My invention, therefore, resides not in any one of these features per se, but rather in the particular combination of all of them herein disclosed. It is distinguished from the prior art in this particular combination of all of its structures for the functions specified.

In order that the detailed description of the invention may be better understood and that the present contribution to the art can be more fully appreciated, additional features of the invention will be described hereinafter. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention.

Further, the purpose of the foregoing abstract" is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application nor is it intended to be limiting as to the scope of the invention in any way.

Accordingly, it is an object of my version of the invention to provide a low-cost, easy-to-manufacture, and easy-to-market movable and adjustable stand for medical cast cooler.

A further object, of my version of the invention is to provide an easy-to-use and versatile movable and adjustable stand for medical cast cooler.

A significant object of the invention is to provide a movable and adjustable stand for medical cast cooler that is comprised of a cylindrical container and a height-adjustable pedestal, the container having an open top and enclosing a cavity that receives and medical cast cooler, said container attached on the bottom side thereof to a top end of the pedestal; the container further comprised of a continuous lateral sidewall attached at the exterior edge of a disc-shaped bottom sidewall, the lateral sidewall bisected into first and second sidewall members that are attached to each other in mirror arrangement by hinges so that the first sidewall member can open and close with respect to the second sidewall member, which remains fixed to the disc-shaped sidewall and possessing an aperture to receive the flexible tube of an medical cast cooler; and the pedestal further comprised of a lower tubular member, an upper tubular member attached at a first end thereof to the bottom side of the bottom sidewall of the container and telescopically received at a second end thereof into the interior of the lower tubular member at a first end thereof, a locking collar located at the junction of the upper and lower tubular members, and a base with wheels, said base attached to the second end of the lower tubular member A final but very significant object of the invention is to provide a movable and adjustable stand for medical cast cooler that contains and supports an medical cast cooler above a floor, ground, or support surface so that the medical cast cooler and stand can be moved relocated over the floor, ground, or support surface to accommodate the movement of a patient without the medical cast cooler's being toppled or tipped over during use, and for the stand to be adjusted in height so that the medical cast cooler can be aligned in the most optimum position with respect to an medical cast while the medical cast cooler is connected thereto.

For a better understanding of the invention, its operating advantages and the specific objects attained by its uses, reference should be made to the accompanying drawings and descriptive matter in which there is illustrated a preferred embodiment of the invention. The foregoing has outlined some of the more pertinent objects of the invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention illustrated by the accompanying drawings.

BRIEF DESCRIPTION OF THE DRAWINGS

The foregoing and other objects, features and advantages of the, invention will become more fully understood from the following description of the preferred-embodiment of the invention as illustrated in the accompanying drawings in which like reference characters refer to the same parts throughout different views. The drawings are not necessarily to scale, emphasis instead being placed upon illustrating the principles of the invention.

FIG. 15c is a cutaway view of the cooler.

DESCRIPTION OF THE PREFERRED EMBODIMENT

Description

Figure 1:
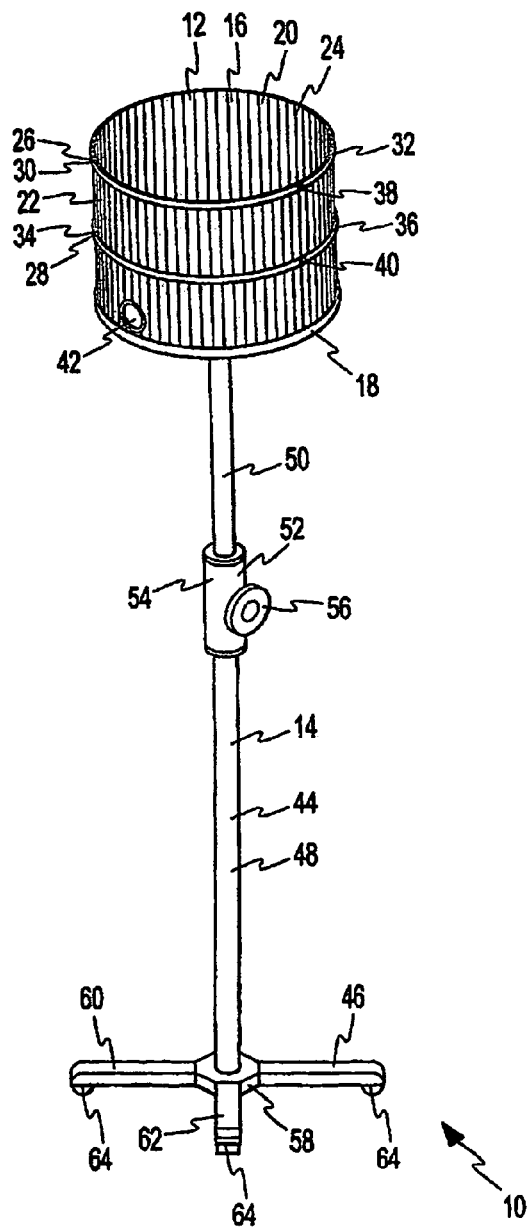
FIG. 1 is a front perspective view of a movable and adjustable stand for medical cast cooler in accordance with the present version of the invention.

Referring now to the drawings and, in particular, to FIG. 1 wherein there is illustrated a typical embodiment of the movable and adjustable stand for medical cast cooler 10. The present version of the invention 10 is comprised of a cylindrical container 12 and a pedestal 14, the container 12 on the bottom side thereof attached to the top end of the pedestal 14. In this manner, the container 12 is maintained at some distance above a ground, floor, or support surface. The container 12 consists of a continuous, lateral sidewall 16 and a circular bottom sidewall 18 with a bottom edge of the lateral sidewall 16 located at the exterior edge of the bottom sidewall 18. The lateral sidewall 16 and bottom sidewall 18 enclose or form a cavity 20. The lateral sidewall 16 is further comprised of a first sidewall member 22 and a second sidewall member 24, said sidewall members 22, 24 generally identical in size and shape.

Figure 2:
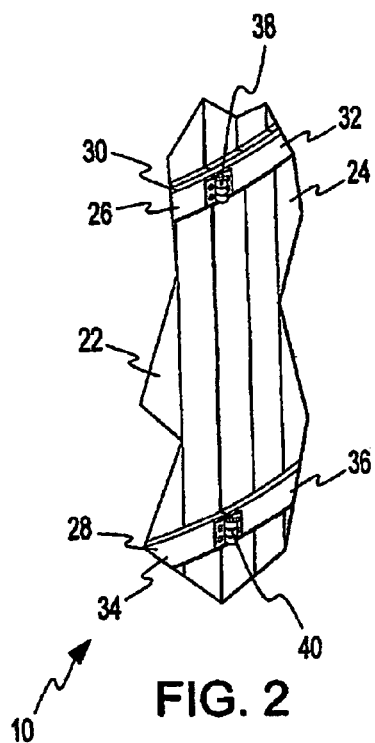
FIG. 2 is a detailed, fragmentary view of hinges located on the exterior of the movable and adjustable stand for medical cast cooler.
Figure 3:
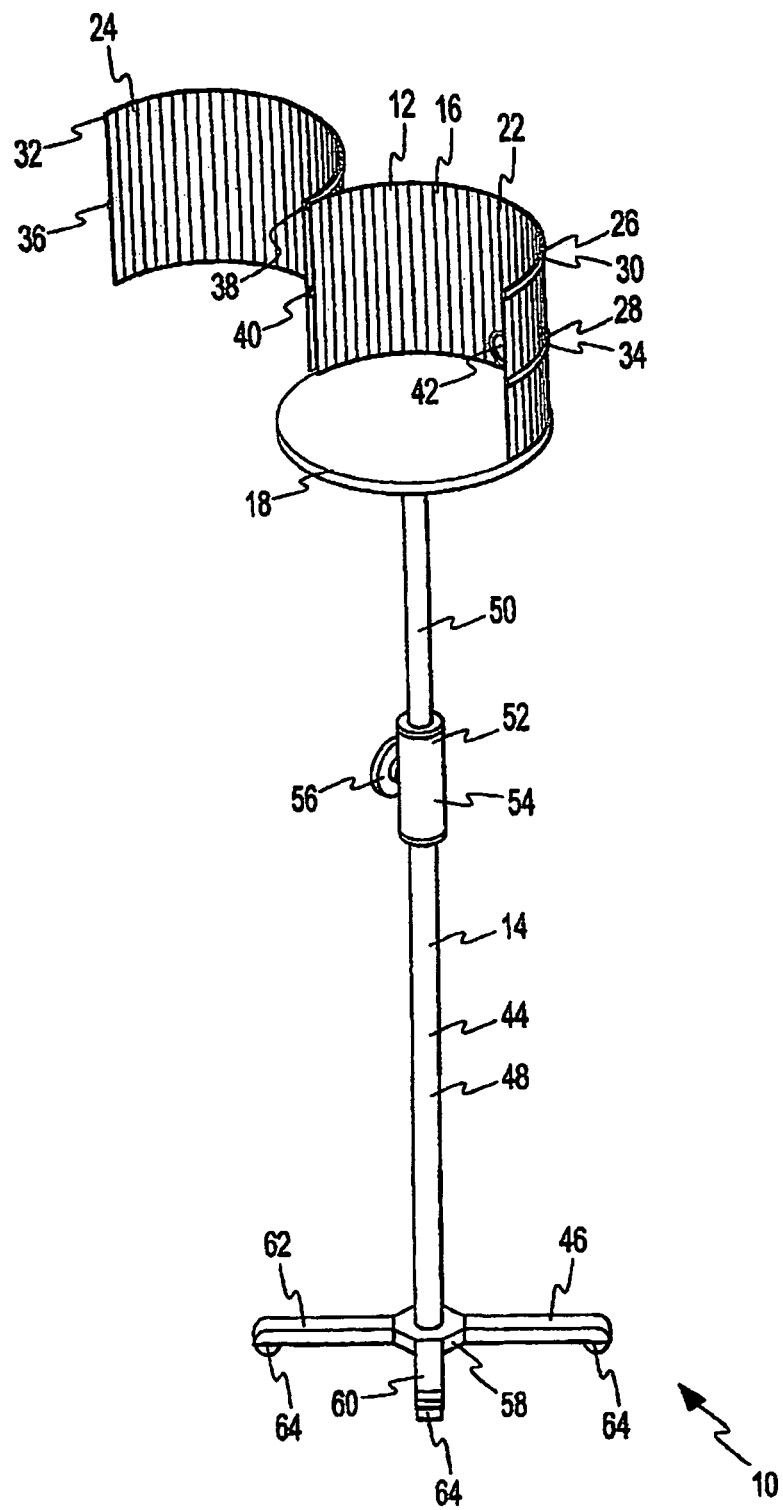
FIG. 3 is a rear perspective view of the movable and adjustable stand for medical cast cooler, illustrating a sidewall member pivoted open to allow access to the interior therein.

A first band 26 surrounds and is connected to the lateral sidewall 16 at a top edge thereof, and a second band 28 surrounds and is connected to the lateral sidewall 16 at the medial section thereof. The first band 26 is comprised of a first band section 30 that is attached to the first sidewall member 22 and a second band section 32 that is attached to the second sidewall member 24. The second band 28 is comprised of a second band section 34 that is attached to the first sidewall member 22 and a second band section 36 that is attached to the second sidewall member 24. The first 30 and second 32 band sections of the first band 26 are attached at cooperating ends to a first hinge 38, and the first 34 and second 36 band sections of the second band 28 are attached at cooperating ends to a second hinge cooperating ends to a second hinge 40. This construction is illustrated in more detail in FIG. 2. At opposing ends of the first section and the second section are removably engaged as shown in FIG. 3 wherein the cooler can be inserted into the interior cavity of the container.

An aperture 42 is located within the container 12, specifically within the first sidewall member 22 of the lateral sidewall 16 at the junction of the first sidewall member 22 and the bottom sidewall 18. The container 12' receives in the cavity 20 thereof and medical cast cooler jug, and the tube of the jug, which is attached to an medical cast, extends through the aperture 42.

Referring again to FIG. 1, the pedestal 12 is comprised of an upright tubular assembly 44 and a base 46. The tubular assembly 44 is further comprised of a lower tubular member 48, a upper tubular member 50, and a locking collar 54. The lower tubular member 48 and upper tubular member 50 are telescopically engaged with the upper:tubular member 50 received within the lower tubular member 48. As such, the upper tubular member 50 can be extended or retracted, with respect to the lower tubular member 48. The container 12, attached at the bottom sidewall 18 thereof to the top end of the upper tubular member 50, is thus raised or lowered in response to extension or retraction of the upper tubular member 50. The locking collar 52 is comprised of a—tubular member 54 and a rotatable handle 56. The tubular member 54 is attached to the top end of the lower tubular member 48 and receives the lower end of the upper tubular member 50 as said tubular member 50 is extended from or retracted, into the lower tubular member 48. The rotatable handle 56 is connected to a pin or similar device that makes contact with the lower tubular member 50 as the handle 56 is rotated in a particular direction, locking said tubular member 50 in. place with respect to the lower tubular member 48 once said tubular member 50 and container 12 are adjusted to an appropriate height above a floor, ground, or support surface.

The base 46, attached medially to the bottom end of the lower tubular member 48, is comprised of a central hub 68 and two cross members 60, 62, which are disposed in perpendicular relation to each other 60,62. Wheels 64 are located within the undersides of the cross members 60, 62 at opposed ends thereof.

Referring to FIG. 3, therein illustrated is the movable and adjustable stand for medical cast cooler 10 showing the rear side thereof. The second sidewall member 24 is pivoted open upon hinges 38, 40 and away from the first sidewall member 22, which remains attached to the bottom sidewall 18, to reveal the interior of the container 12. Second band sections 32, 36, which are connected to the second sidewall member 24, are also separated from first band sections 30, 34, which are connected to the first sidewall member 22, respectively. The bottom sidewall 18 is fully exposed and accessible as necessary to position an medical cast cooler jug within the container 12 upon the bottom sidewall 18.

Figure 4:
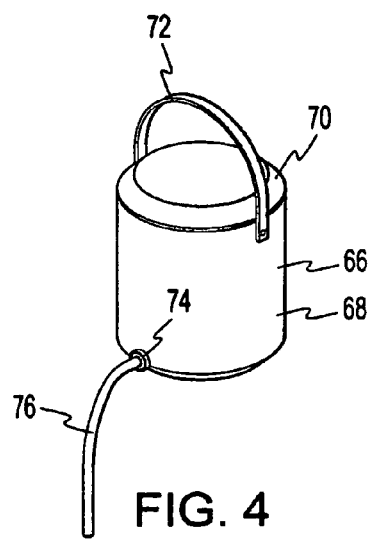
FIG. 4 is a front perspective view of an medical cast cooler jug.
Figure 5:
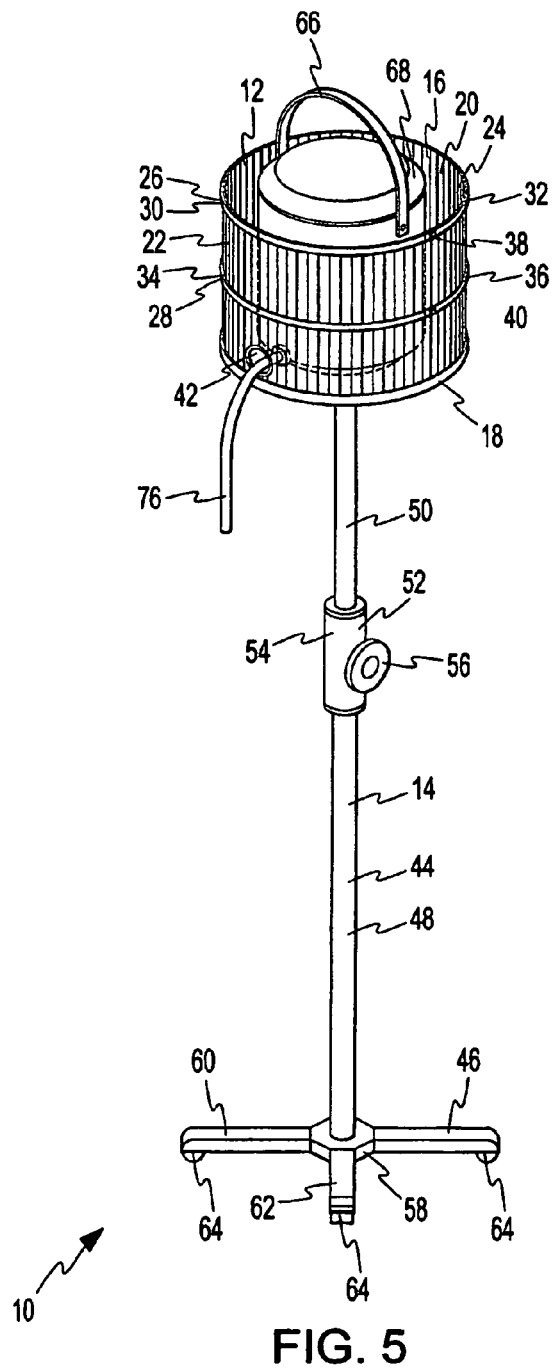
FIG. 5 is a front perspective view of the movable and adjustable stand for medical cast cooler with the medical cast cooler jug situated therein.

A typical medical cast cooler jug 66 is illustrated in FIG. 4. The jug 66 is comprised of a hollow, cylindrical container 68, detachable lid 70, and handle 72 pivotally attached to the top side of the container 68. A collar 74 is located on the container proximate to the bottom end thereof and surrounds a flexible hose 76 extending from said collar and contiguous section of container 68. The flexible hose 76 is hollow and transports coolant solution, typically ice water stored within the container 68, from the container 68 to an medical cast (not shown) worn by a patient. As illustrated in FIG. 5, the medical cast cooler jug 66 is situated within the cavity 20 of the container 12. More specifically, the container 68 of the jug 66 is resting upon the bottom sidewall 18 and is enclosed by the lateral sidewall 16. The flexible hose 76 extends from the container 68 of the jug 66 through the aperture 42 of the first sidewall member 22 of the cooler container 12. As such, stand 10 supports the jug 66 above a floor, ground, or support surface while the free end of the hose 76, extending from the container 68 of the jug 66 at a first end thereof, can be attached to an medical cast (not shown) at a second, free end thereof. Cooling solution stored within the container 68 of the jug will be transported by force of gravity from the container 68 of the jug 66 through the flexible hose 76 and ultimately to the medical cast to provide simultaneous cold and compression therapy to the skin, muscles, and other tissue encased within the medical cast.

Figure 6:
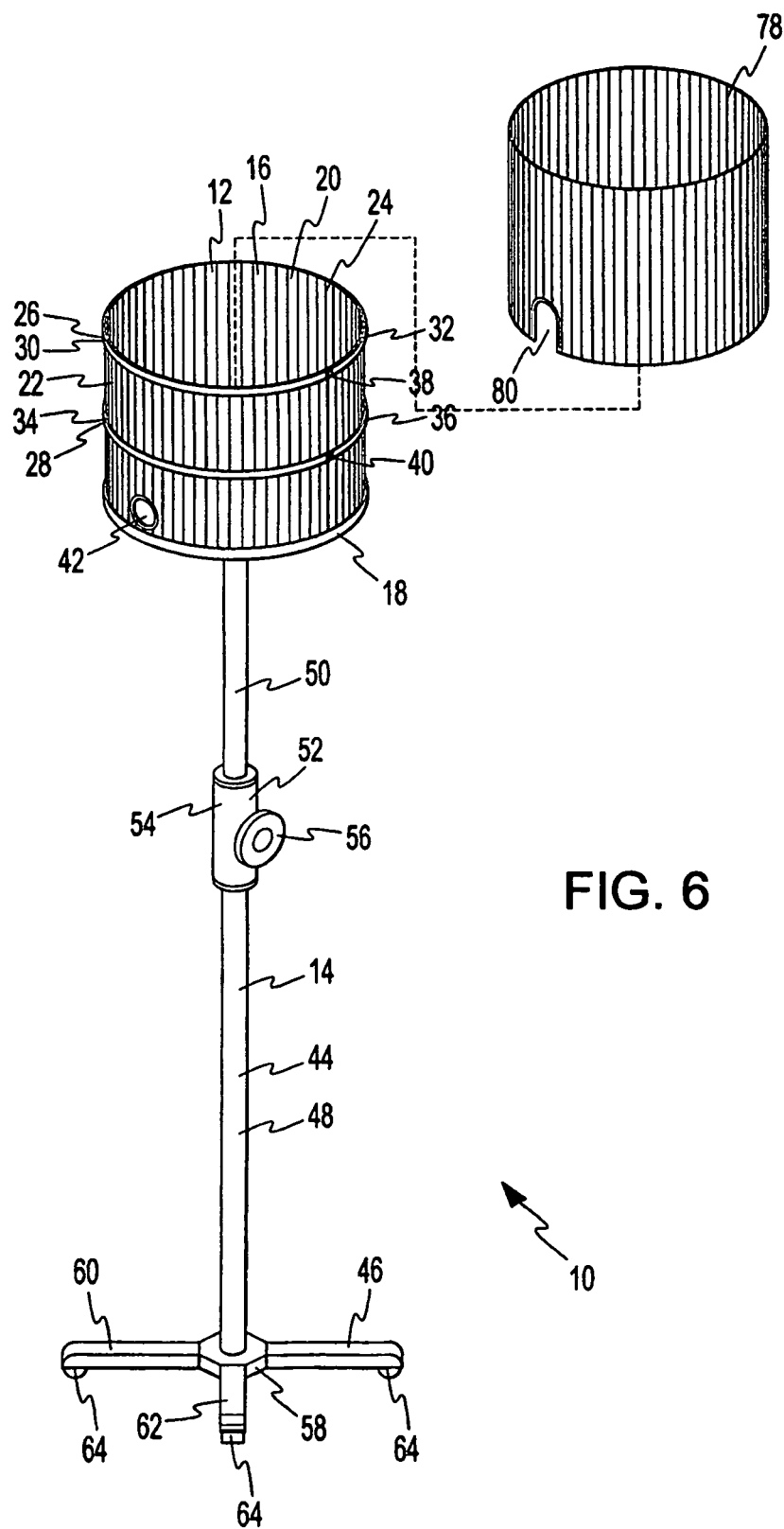
FIG. 6 is a front perspective view of the movable and adjustable stand for medical cast cooler with an extensible sidewall aligned for insertion therein.
Figure 7:
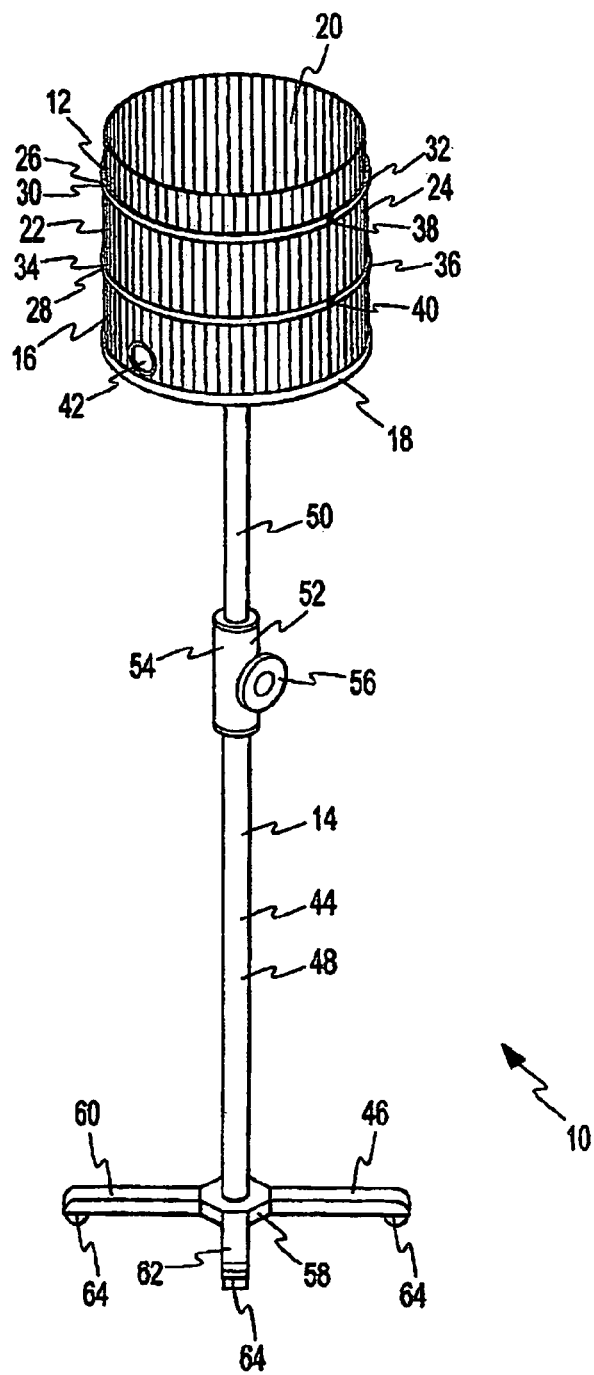
FIG. 7 is a front perspective view of the movable and adjustable stand for medical cast cooler with the extensible sidewall situated therein.

The medical cast cooler stand 10 can be modified or customized with various accessories or devices to-enhance and improve its functionality in a various applications. In FIG. 6, for instance, the medical cast cooler stand 10 is illustrated with an extensible sidewall 78 aligned for insertion into the container 12 of the stand 10 so that the exterior sidewall is located adjacent to and enclosed by the lateral sidewall 16. The extensible sidewall 78 is a circular! and continuous in shape so as to conform to the shape of the lateral sidewall 16. An indentation 80 is located along the bottom edge of the extensible sidewall 78 and is aligned with the aperture of the lateral sidewall 16 of the container 12 when the extensible sidewall 78. is inserted therein. As illustrated in FIG. 7, the extensible sidewall 78 is inserted within the lateral sidewall 16 of the container 12 with the top edge of the extensible sidewall 78 extending above the top edge of the lateral sidewall 16. The extensible sidewall 78 can be raised or lowered with respect to the lateral sidewall 16 so as to increase the holding capacity of the container 12 as necessary to accommodate cooler jugs of varying size and capacity. The outer surface of the extensible sidewall 78 makes slight frictional engagement with the inner surface of the lateral sidewall 16 as necessary to maintain the extensible sidewall 78 in position against the lateral sidewall 16 when the extensible sidewall 78 is raised or lowered as needed. When the extensible sidewall 78 is lowered within the container 12 against the lateral sidewall 16 thereof, the indentation 80 aligns with the aperture 42 in order to permit the flexible tube 76 of the container jug 66 to extend out and from the container 12.

Figure 8:
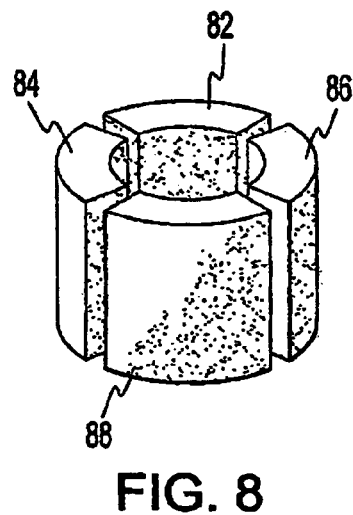
FIG. 8 is a perspective view of a series of resilient spacer pads.
Figure 9:
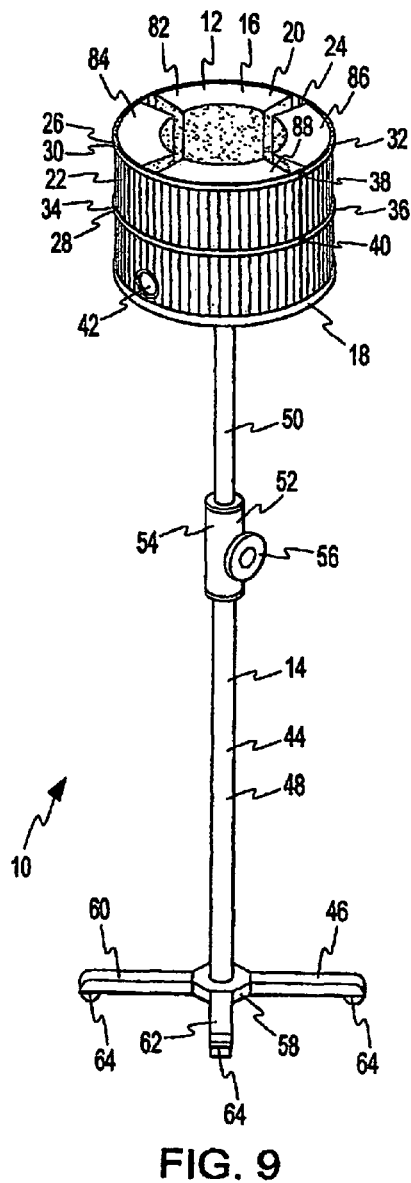
FIG. 9 is a front perspective view of the movable and adjustable stand for medical cast cooler with the series of resilient spacer pads situated therein.

In FIG. 8, therein is illustrated a series of flexible, resilient pads 82, 84, 86, 88. The pads 82, 84, 86, 88 are comprised of compressible, resilient material, such as rubber, foam, and the like and are inserted into the container 12 of a cooler stand 10 to occupy any space that may exist between the exterior surface of the container of the cooler jug and inner surface of the lateral sidewall 16 of the container 12 in order to prevent the cooler jug from becoming displaced from an optimum or initial position within the container 12. The pads 82, 84, 86, 88, when configured as illustrated, form a central space or area that can be occupied by a cooler jug. As displayed in FIG. 9, the pads 82, 84, 86, 88 are inserted into the container 12 of the stand 10 with the exterior sides of the pads 82, 84, 86, 88 making contact with the inner surface 30 of the lateral sidewall 16 of the container 12. The central or inner space formed by the pads 82, 84, 86, 88 can be occupied by a cooler jug, and any space between the cooler jug and inner surface of the lateral sidewall 16 of the container 12 is taken up by the pads 82, 84,86,88. In this manner, the cooler jug can be prevented from sliding, moving, or otherwise being displaced from its original or optimal position within the container 12.

Figure 10:
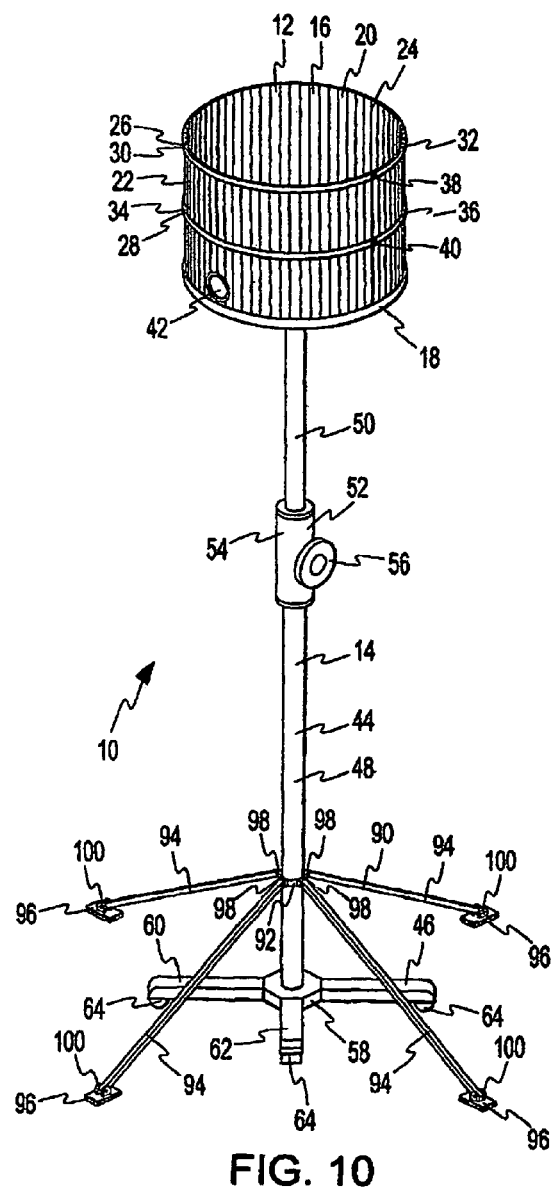
FIG. 10 is a front perspective view of the movable and adjustable stand for medical cast cooler with an accessory outrigger stand attached thereto.

In FIG. 10, the cooler stand 10 is illustrated with an outrigger stand 90 releasably attached to the lower tubular member 48. The outrigger stand 90 can be fitted temporarily or permanently to the cooler stand 10 to improve the stability of the cooler stand 10 as necessary. Additional stability for the cooler stand 10 may be required, for instance, when the upper tubular member 50 is fully extended from the lower tubular member 48, when the capacity of the cooler jug positioned within the container 12 is larger than normal, or when the environment in which the cooler. stand 10 is being used may subject the cooler stand 10 to conditions that may reduce or otherwise negatively affect the stability of the cooler stand 10. The outrigger stand 90 is comprised of a central collar 92 that is positioned around the lower tubular member 48, four narrow, elongate legs 94 that extend from the central collar 92 approximately every 90 degrees of arc, and footpads 96. Each leg 94 is pivotally attached at a first end to a cooperating hinge on the collar 92 and pivotally attached at a second end to a cooperating hinge on a respective footpad. In this manner, the legs 94 can be individually raised' or lowered with respect to the collar 92, and each footpad 96 can be pivoted upon a leg 94 to conform to a floor, ground, or support surface.

Figure 11:
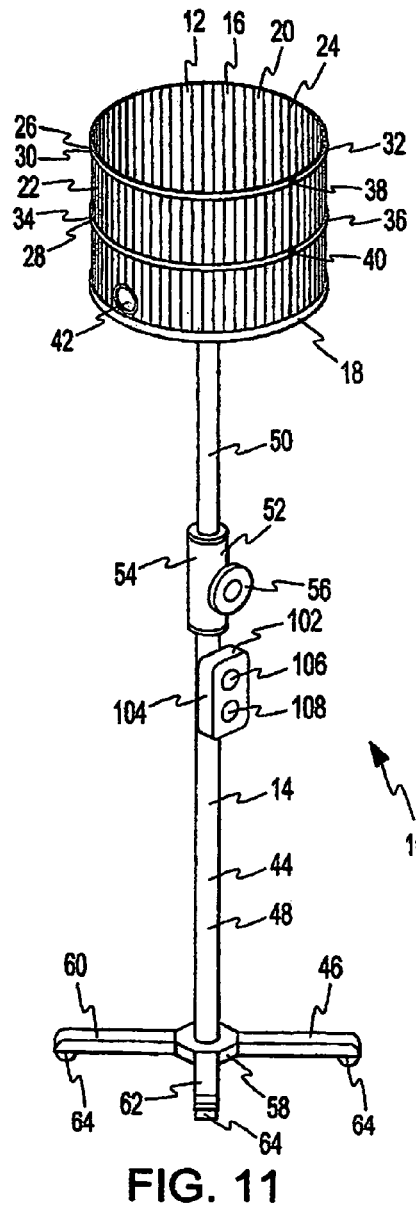
FIG. 11 is a front perspective view of the movable and adjustable stand for medical cast cooler with a motion sensor and alarm attached thereto.

In FIG. 11, the cooler stand 10 is fitted on the lower tubular member 48 of the pedestal 14 thereof with a motion sensor and alarm 102. The sensor 102 detects and notifies by alarm signals a user of any movement or motion that could cause the cooler stand 10 to tip over and fall. The motion sensor and alarm 102 is comprised in part of an exterior housing that contains motion sensing circuitry and power source well known in prior art and design, a visual alarm 106, such as a blinking light source, and an audible alarm 108, such as a buzzer, ringer, or the like.

Figure 12:
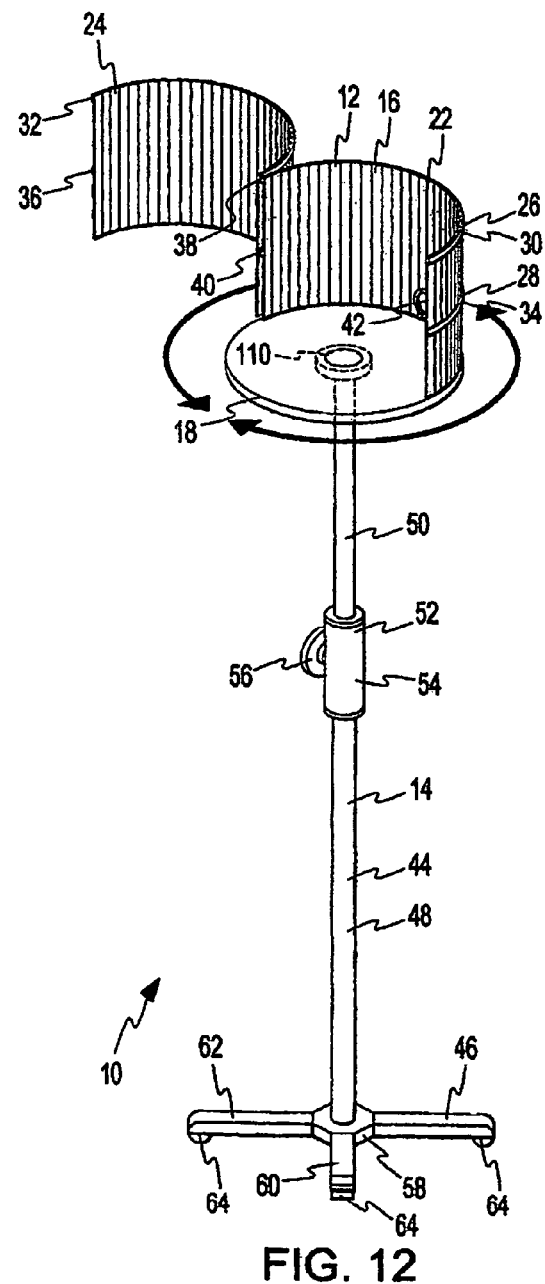
FIG. 12 is a rear perspective view of the movable and adjustable stand for medical cast cooler, illustrating a sidewall member pivoted open and a swivel hinge located between the pedestal and container of said stand.
Figure 13:
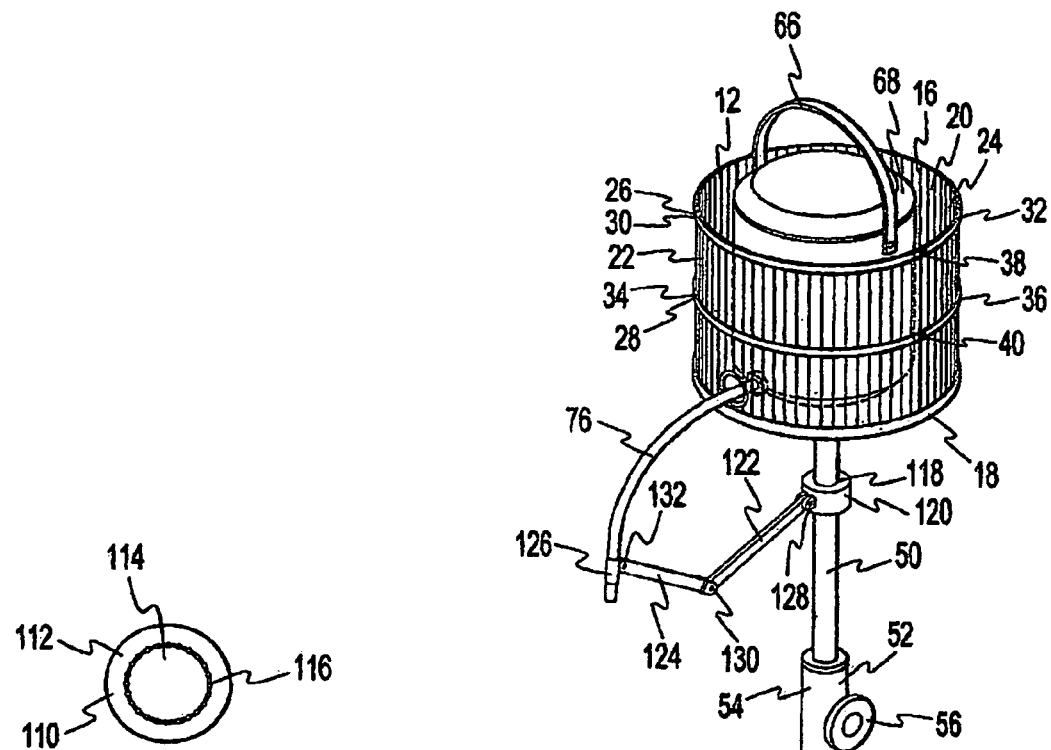
FIG. 13 is a detailed, elevation view of the swivel hinge.

In certain applications, it becomes necessary to reposition or reorient the cooler jug 66 or flexible tube 76 so that the flexible tube 76 can accommodate the location, position, or attitude of the user wearing an medical cast, to which the flexible tube is attached. In some cases, the cooler jug 66 can be repositioned by moving the cooler stand 10 upon the wheels 64, or the upper tubular member 50 can be extended or retracted within the lower tubular member 48, as described previously. In some situations, however, it may be difficult or impossible to relocate the cooler stand 10 upon its wheels 64 or adjust the height of the tubular assembly 44 because of cramped quarters, intervening furniture, clutter, and the like. One alternative to relocating or moving the entire cooler stand 10 is to rotate or reorient the container 12 so that the direction and orientation of the flexible tube 76 can be re-aligned. As shown in FIG. 12, a rotatable or swivel hinge 110 (shown in phantom line) is attached on a first side thereof to the top of the upper tubular member 50 and on an opposed second side to the bottom side of the bottom sidewall 18. As such, the container 12 can be rotated with respect to the pedestal 14 as shown by directional arrows. The swivel hinge 110, illustrated in more detail in FIG. 13, is comprised 30 of a ring-shaped outer band 112 and a disc-shaped inner hub 114. A series of ball bearings 116 is located partially within the outer edge of the of the hub 114 and inner edge of the outer band 112, thereby permitting the outer band 112 to rotate with respect to the hub 114. The swivel hinge 110 is thus secured to the cooler stand 10 by means of the outer band 112 attached at a first side thereof to the bottom side of the bottom sidewall 18 and the hub 114 attached at an opposed second side thereof to the top of" the upper tubular member 50.

Figure 14:
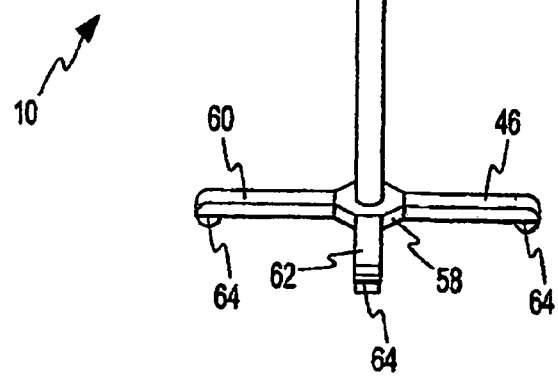
FIG. 14 is a front perspective view of the movable and adjustable stand for medical cast cooler with a tube support arm 15 attached thereto.

Referring to FIG. 14, therein illustrated is the medical cast cooler stand 10 with a tube support arm 118 releasably attached to the upper tubular member 50 between the bottom sidewall 18 and collar 52. The tube support arm 118 is comprised of a first collar 120, first arm 122, second arm 124, and second collar 126. The first arm at a first end thereof is pivotally attached to the first collar 120 at hinge 128 and at an opposed second end pivotally attached to a first end of the second arm 124 at hinge 130. The second arm 124 at a second end opposed to the first end' attached to the first arm 122 is pivotally attached to the second collar. 126 at hinge 132. The second collar 126 as illustrated contains the free end of the flexible tube 76. In this manner, the second collar and cooperating end of the flexible tube 76 can be retracted to and from the upper tubular member 50 and container 12 and can be raised or lowered with respect to the upper tubular member and container 12. The tube support arm 118' thus functions to maintain the end of the flexible tube 76 in various positions as necessary to ensure the continued and uninterrupted flow of cooling solution from the cooler 66 to the medical cast (not shown).

Figure 15:
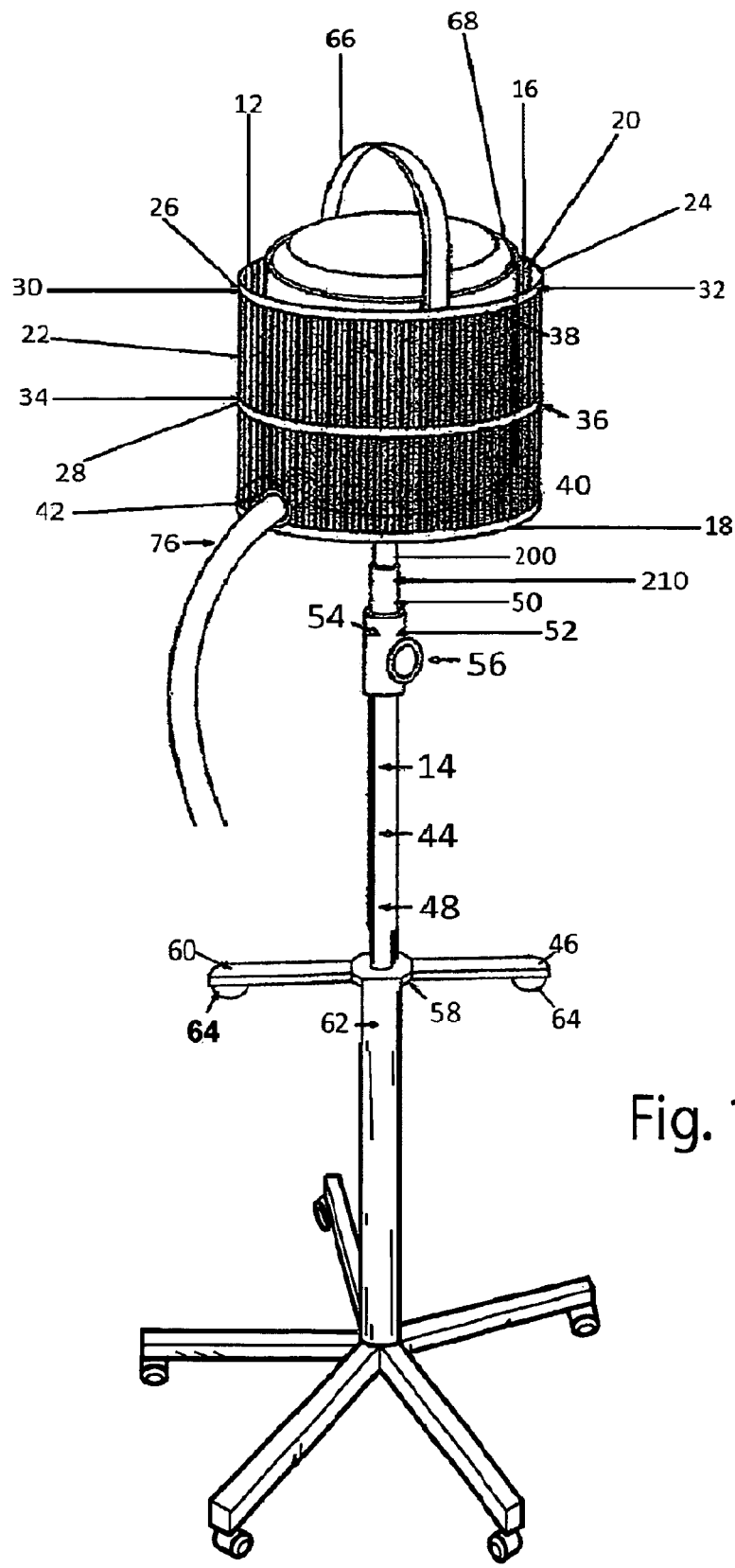
FIG. 15 is an alternative embodiment to the equipment stand.
Figure 16:
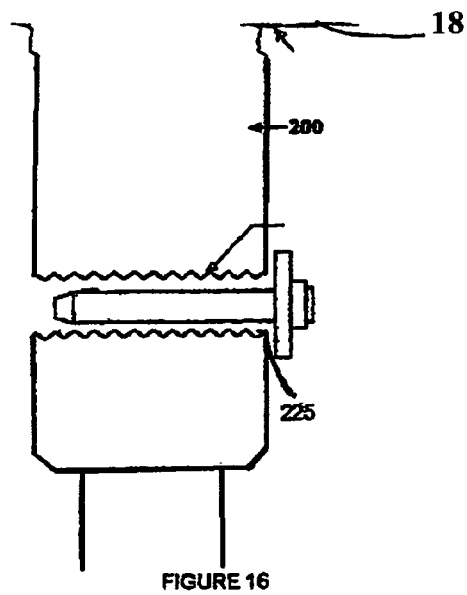
FIG. 16 illustrates an enlarged side view of the base of the cylindrical container with a locking pin inserted.
Figure 17:
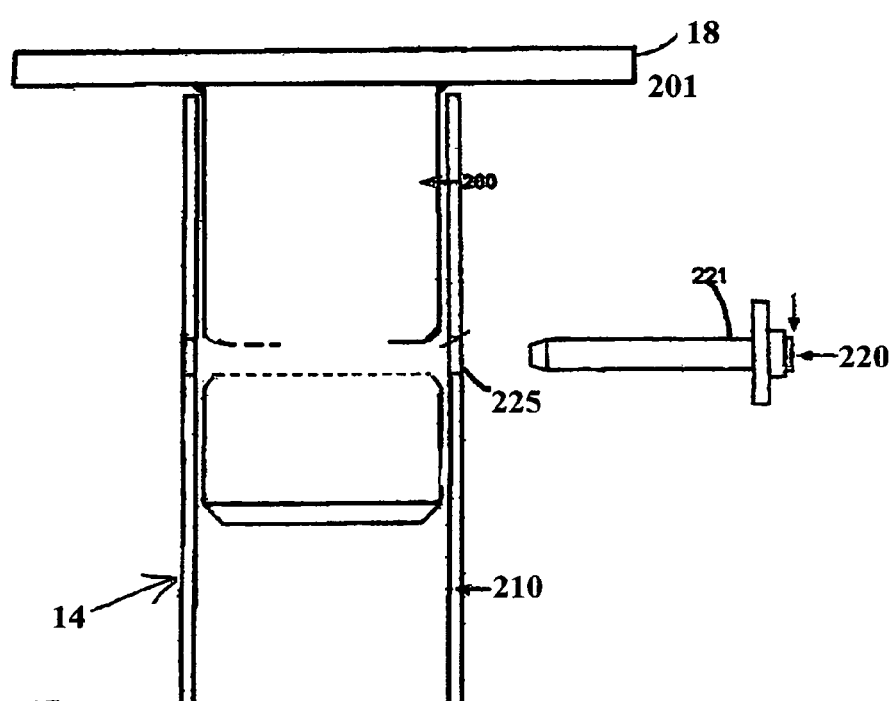
FIG. 17 illustrates an enlarged side view of the base of the cylindrical container with a locking pin removed.
Figure 18:
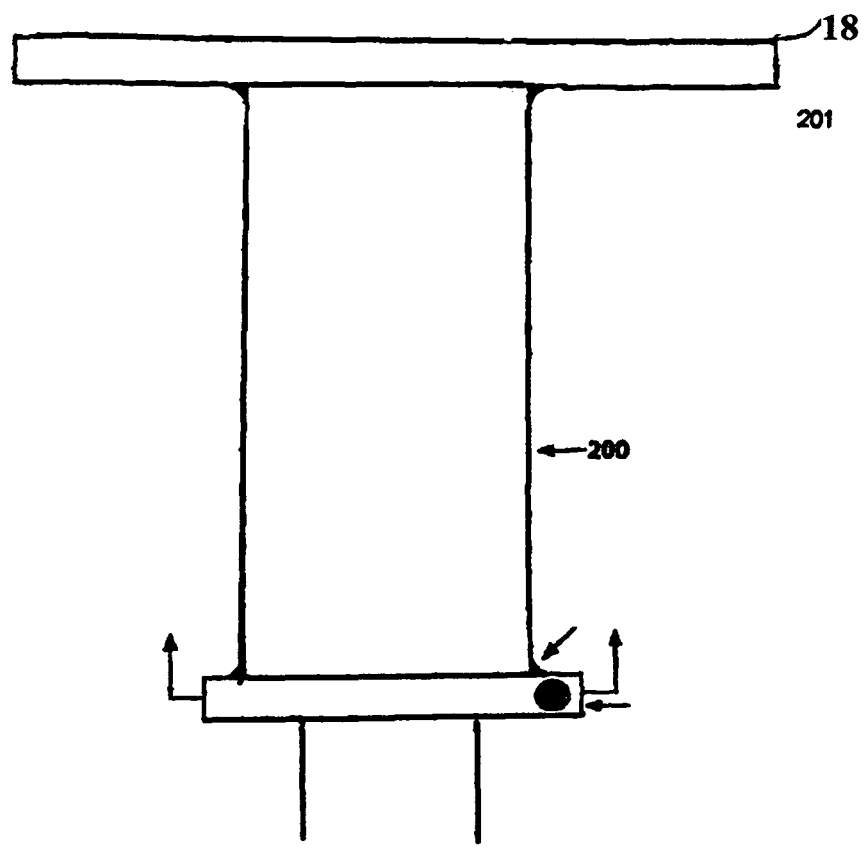
FIG. 18 illustrates a frontal view of the pedestal with the pin inserted.
Figure 19:
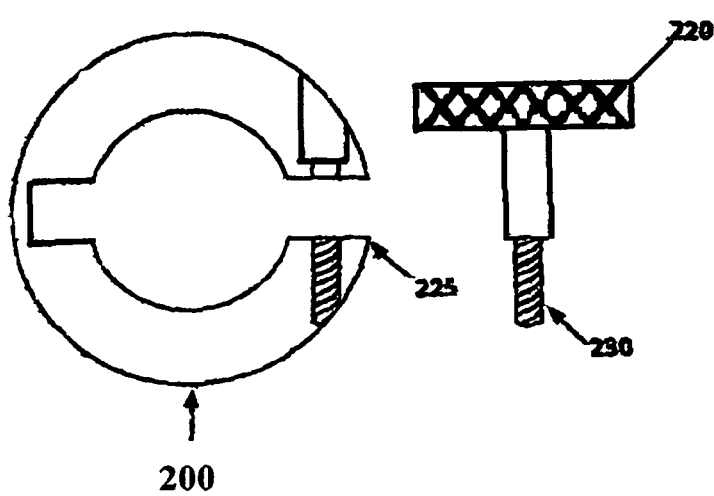
FIG. 19 illustrates an enlarged view of the pedestal. 13

Referring to FIG. 15 in an alternative embodiment of the present invention, cylindrical container 12 can be removable attached to pedestal 14. Referring to FIGS. 16, 17, 18, and there is depicted an enlarged view of the connection between the cylindrical container 12 and pedestal 14. The bottom side of cylindrical container 12 is adapted with adapted with a shaft 200 which extends linearly downward therefrom. The upper end 210 of pedestal 14 is hollow therethrough thereby allowing for the insertion of shaft 200 therein. Locking mechanism 56 secures shaft 200 in place locking mechanism further includes bore 202 and pin 220. As depicted, at a predetermined location, bore 225 extends horizontally through shaft 200. Bore 225 is adapted with threads to secure pin 220 in place. On opposing sides of the upper end 210 of pedestal 14 are apertures aligned with bore 225. Pin 220 is adapted with a release mechanism 221 for the removal of pin 220 from aperture 202.

Figure 15A:
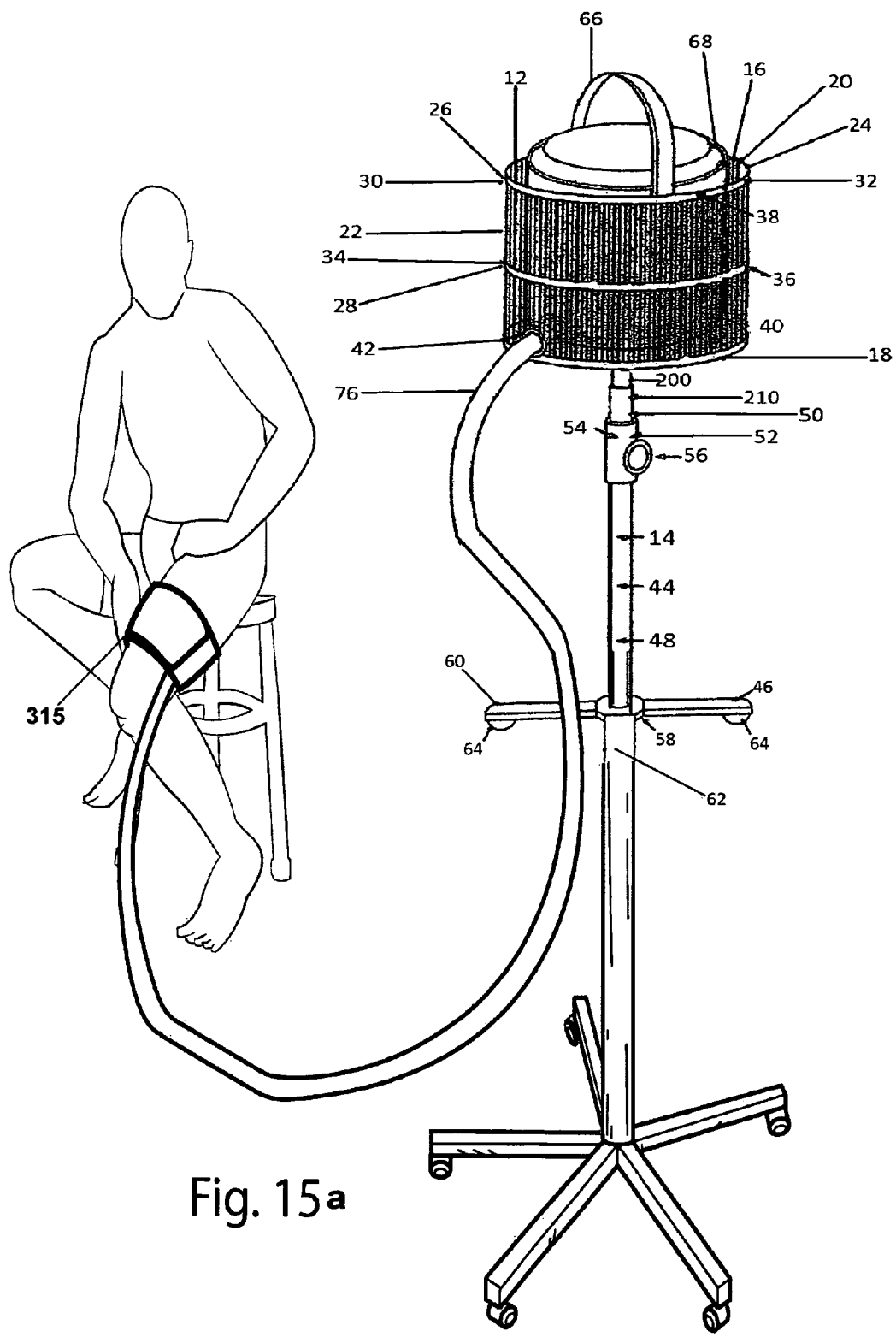
FIG. 15a illustrates a medical cuff attached to a user's body.
Figure 15B:
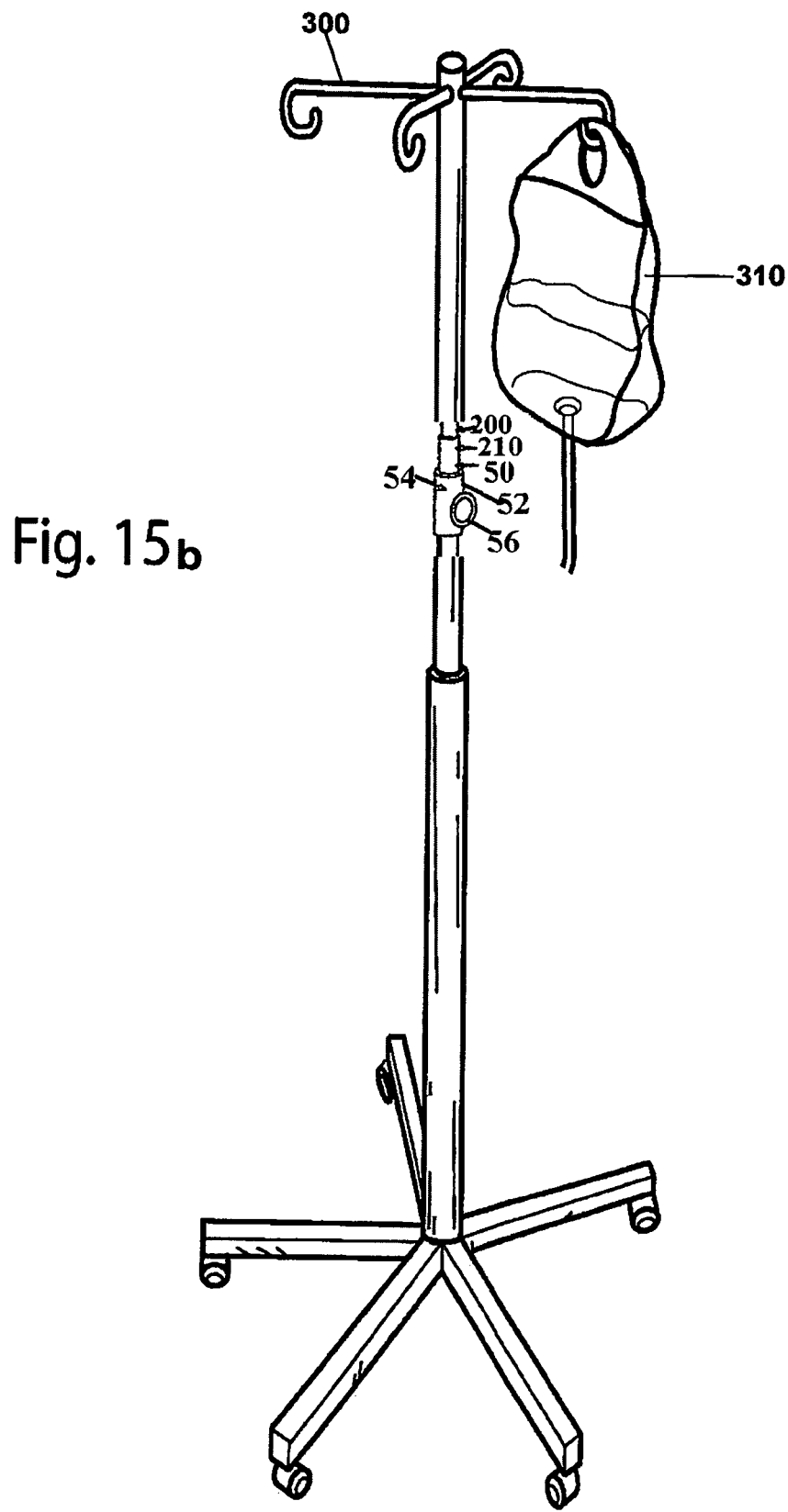
FIG. 15b illustrates top end attached to IV stand.
Figure 15:
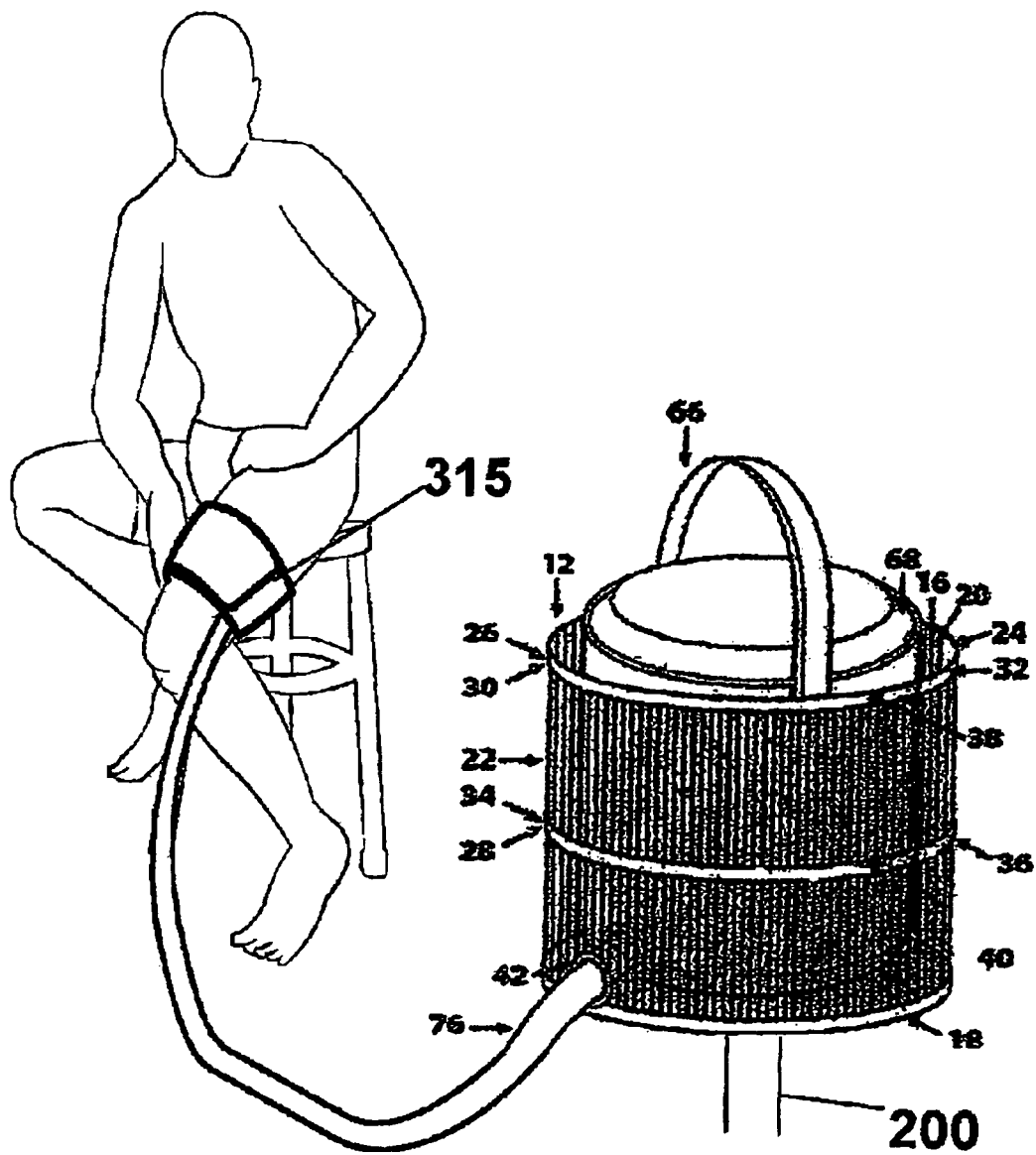
Figure 15D:
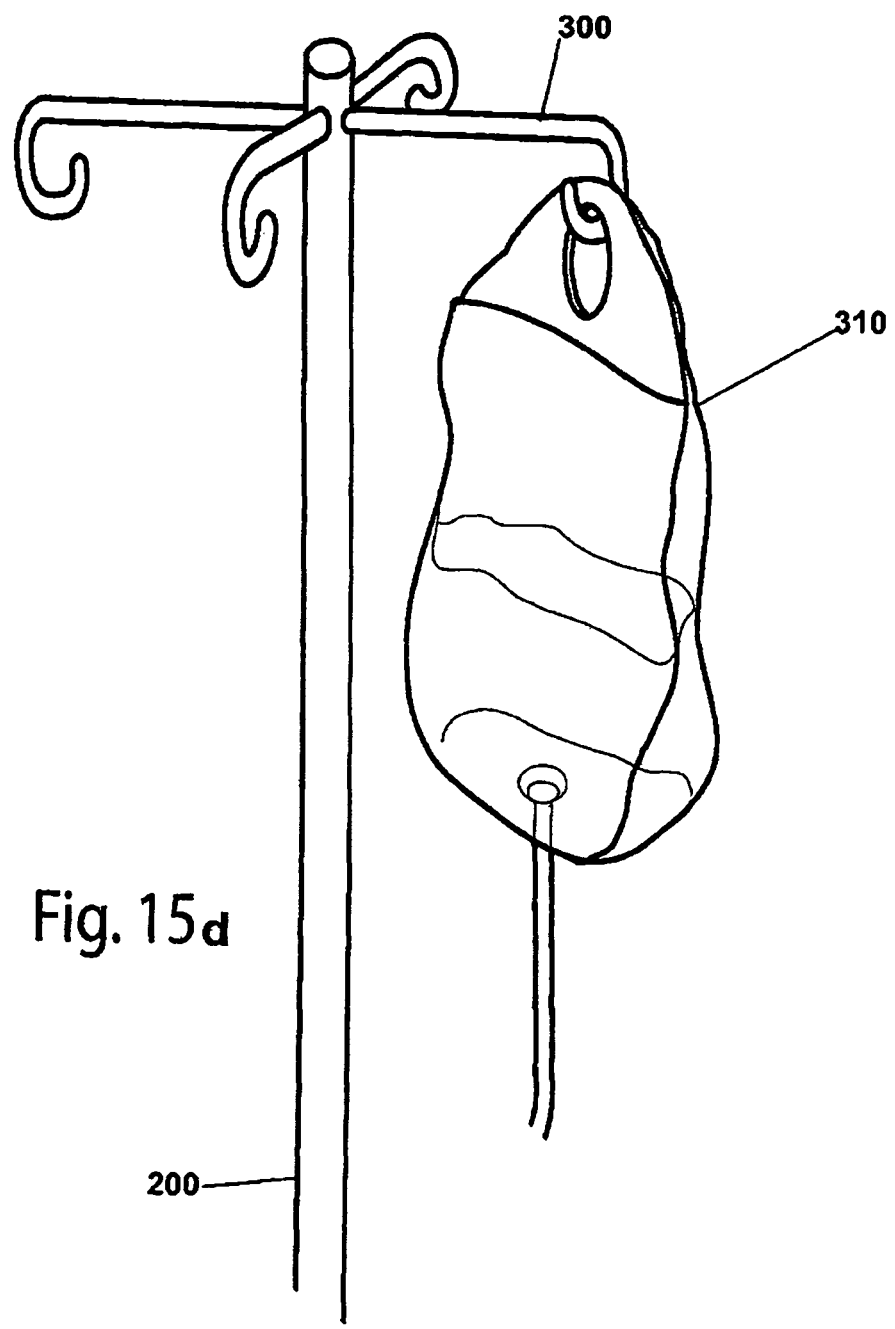
FIG. 15d is a cutaway view of IV stand.

The removal of cylindrical container 12 from pedestal 14 allows the stand to be used interchangeable for other uses. In the alternative embodiment the base of an Intravenous (IV) stand can be adapted with shaft 200 thereby allowing for the insertion and removal of the IV into the upper end of 210 of pedestal 14. FIG. 15 illustrates the container (12) with shaft member (200) attached to the bottom side of wall (18) of container (12). FIG. 15a shows tube 17 attached to medical cuff (315) for delivery of a cooling solution from cooler 66 through tube 76 into cuff (315). FIG. 15b shows IV stand upper portion being interchangeable upon pedestal 14. IV Stand has shaft 200 which inserts 210. As shown IV the stand comprises a shaft member (200) with IV hooks perpendicularly attached to the upper end of shaft 200. FIG. 15c shows a cutaway view of the interchangeable container of the present invention. FIG. 15d shows a cutaway view of the interchangeable IV stand of the present invention.

While this version of the invention has been illustrated and described in detail in the drawings and foregoing description, the same is to be considered as illustrative and not restrictive in character, it being understood that only the preferred embodiment has been shown and described and that all changes and modifications that come within the spirit of the version of the invention are desired to be protected. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

All changes and modifications that come within the spirit of the version of the invention. are desired to be protected. With respect to the above description then, it is to be realized that the optimum dimensional relationships for the parts of the invention, to include variations in size, materials, shape, form, function and manner of operation, assembly and use, are deemed readily While this version of the and described in detail in description, the same is to be not restrictive in character, the preferred embodiment has, be invention has been illustrated the drawings and foregoing considered as illustrative and it being understood that only en shown and described and that all changes and modifications that come within the spirit of the version of the invention are desired to be protected. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Conclusion and Scope of Invention

From the foregoing, it will be understood by persons skilled in the art that an improved movable and adjustable stand for medical cast cooler has been provided. The invention is relatively simple and easy to manufacture, yet affords a variety of uses. While my description-contains many specificities, these should not be construed as limitations on the scope of the version of the invention, but rather as an exemplification of the preferred embodiment thereof. The foregoing is considered as illustrative only of the Principles of the invention. Further, since numerous modifications and changes will readily occur to those skilled in the art, it is not desired to limit the invention to the exact construction and operation—shown and described, and accordingly all suitable modifications and equivalents may be resorted to, falling within the scope of the invention. Although this invention has been described in its preferred form with a certain degree of particularity, it is understood that the present disclosure of the preferred" form has been made only by way of example and numerous changes in the details 'of construction and combination and arrangement of parts may be resorted to without departing from the spirit and scope of the invention.

What is claimed is:

1. An interchangeable medical equipment stand in combination with a cooler, the stand comprising:
a cylindrical container having a bottom side, and a surrounding lateral sidewall; the lateral sidewall extending linearly upward from the bottom side to an opened top edge forming an interior cavity wherein the cooler containing a solution which drains through an attached hose tubing in fluid communication with a medical cuff surrounding a bodily injury is contained therein; an elongated pedestal defined by a top end and a bottom end, the top end being attached underneath the bottom side of the container; a base attached to the bottom end of the pedestal, wherein the container is supported in an upright position a distance above the surface of a ground; and an aperture in the lateral side wall of the container above the bottom side receiving the hose tubing there through.

2. The stand of claim 1 wherein the lateral side wall further comprises:
a first sidewall member and a second sidewall member each having a first end and an opposing end; the first end of the first sidewall member and the first end of the second sidewall member being cooperatively and releaseably engaged; and the second end of the first sidewall member and the second end of the second sidewall member being cooperatively and pivotally engaged wherein the lateral side wall can be opened for placement of the cooler within the interior cavity.

3. The stand of claim 1 wherein the container further comprises a first band that surrounds and connects to the top edge of the lateral side wall.

4. The stand of claim 1 wherein the container further comprises a second band that externally surrounds the lateral side wall at a median point and connects thereto.

5. The stand of claim 3 wherein the lateral side wall further comprises:
a first sidewall member and a second sidewall member each having a first end and an opposing end; the first end of the first sidewall member and the first end of the second sidewall member being cooperatively and releaseably engaged; and the second end of the first sidewall member and the second end of the second sidewall member being cooperatively and pivotally engaged wherein the lateral side wall can be opened for placement of the cooler within the interior cavity; the first band having a first section and a second section; the first section of the first band being attached to the first sidewall member; and the second section of the first band being attached to the second sidewall member.

6. The stand of claim 5 wherein the first section of the first band and the second section of the first band are removably coupled at one side cooperating ends.

7. The stand of claim 4 wherein the lateral side wall further comprises:
a first sidewall member and a second sidewall member each having a first end and an opposing end; the first end of the first sidewall member and the first end of the second sidewall member being cooperatively and releaseably engaged; and the second end of the first sidewall member and the second end of the second sidewall member being cooperatively and pivotally engaged wherein the lateral side wall can be opened for placement of the cooler within the interior cavity;
the second band having a first band section and a second band section;
the first band section being attached to the first sidewall member;
and the second band section being attached to the second sidewall member.

8. The stand of claim 1 wherein the pedestal further comprises:
an upper tubular member having a top end and a bottom end; a lower tubular member having a top end and a bottom end; the top end of the upper tubular member is attached underneath the bottom side of the container; the bottom end of the upper tubular member being telescopically engaged with and received by the top end of the lower tubular member, such that the pedestal can be raised or lowered cooperatively with the extension or retraction of the upper tubular member.

9. The stand of claim 8 wherein the pedestal further comprises:
a locking mechanism operatively coupled to the upper and lower tubular member wherein the upper tubular member can be adjusted and secured in place in relation to the lower tubular member wherein the pedestal can be adjusted to a desired height.

10. The stand of claim 1 wherein the base further comprises:
a central hub having two cross-members which are disposed in perpendicular relation to each other, and wheels located within the undersides of the cross-members at opposed ends thereof.

11. The stand of claim 1 wherein the pedestal further comprises:
an outrigger stand having a central collar and a plurality of elongated narrow leg members; the central collar being positioned around the tubular member; each leg member being defined by a first end and an opposite second end; each leg member being pivotally connected at the first end to the central collar and extending therefrom such that the leg member can be individually raised or lowered with respect to the collar; each leg member being positioned around the central collar approximately every 90 degrees of an arc; a foot pad being pivotally connected to the opposite second end of each leg member such that the foot pad can be pivoted upon a leg to conform to a floor, ground or support surface.

12. The stand of claim 1 wherein the container further comprises:
a circular continuous extensible sidewall which conform to the shape of the lateral side wall; an indentation formed within a bottom edge of the extensible sidewall and aligned with the aperture of the lateral sidewall in order to permit the flexible tubing outlet of the cooler to extend out and from the container; the extensible sidewall having a top edge extending above the opened top edge of the lateral sidewall when the extensible side wall is inserted into the container wherein the extensible side wall can be raised or lowered with respect to the lateral sidewall so as to increase the holding Capacity of the container; the extensible sidewall having a diameter slightly smaller than the container such that an outer surface of the extensible sidewall makes slight fictional engagement with an inner surface of the lateral sidewall to maintain the extensible sidewall in position against the lateral sidewall when the extensible is inserted into the container.

13. The stand of claim 1 wherein the pedestal further comprises a tube support arm attached to the upper tubular member;
the tube support arm having a first arm, a second arm, a first collar, and a second collar; the first arm having a first end and an opposed second end; the second arm having a first end and an opposed second end; the first collar being attached to the upper tubular member; the first end of the first arm being pivotally attached to the first collar; the opposed second end of the first arm being pivotally attached to the first end of the second arm; the opposed second end of the second arm being pivotally attached to the second collar; and the second collar being attached to a free end of the flexible tubing such that the flexible tubing can be retracted to and from the upper tubular member and the container can be raised or lowered with respect to the upper tubular member and the container.

14. The stand of claim 8 wherein the pedestal further comprises:
a motion detector operationally coupled to the lower tubular member, the motion detector having a sensor and an alarm; the sensor for detecting any movement that could cause the cooler to tip over and fall from the cavity of the container; and an alarm operational connected to the sensor, the alarm having means for notifying the user of movement.

15. The stand of claim 8 wherein the pedestal further comprises:
a swivel hinge having a first side and an opposed second side; the first side being attached to the upper tubular member at its upper end; the opposed second side being attached to the bottom side of the bottom sidewall such that the container can be rotated with respect to the pedestal in a particular direction.

16. The stand of claim 1 wherein the container further comprises:
a compressible resilient pad configured to be seated within the cavity of the container; the pad being a geometrical shape having a depth, an interior plane side and an exterior plane side; the interior tide having a recessed portion configured to seat upon the exterior surface of the cooler; and
the depth defined by the space that between the exterior surface of the cooler and the inner surface of the lateral sidewall wherein the cooler is prevented from becoming displaced from an inserted position within the cavity of the container.

17. The stand of claim 1 wherein the container is releaseably engaged from the top end of the pedestal.

18. The stand of claim 17 wherein the top end of the pedestal is removably engaged with a shaft member with IV hooks perpendicularly and radially attached to a top end thereof wherein the medical equipment stand becomes an IV stand.

19. The stand of claim 7 wherein the first band section and the second band section are removably coupled at cooperating ends.

* * * * *